United States Patent
Tomioka et al.

(10) Patent No.: US 7,754,157 B2
(45) Date of Patent: Jul. 13, 2010

(54) HUMIDIFIER

(75) Inventors: Toshikazu Tomioka, Ibaraki (JP); Takahiro Nakajima, Kasugai (JP); Jun Inagaki, Kasugai (JP); Yoshihito Nakanishi, Higashiosaka (JP); Tetsuya Yoshida, Osaka (JP)

(73) Assignees: Panasonic Corporation, Osaka (JP); Panasonic Ecology Systems Co., Ltd., Aichi (JP)

( * ) Notice: Subject to any disclaimer, the term of this patent is extended or adjusted under 35 U.S.C. 154(b) by 1324 days.

(21) Appl. No.: 10/610,796

(22) Filed: Jul. 1, 2003

(65) Prior Publication Data
US 2004/0045909 A1   Mar. 11, 2004

(30) Foreign Application Priority Data
Jul. 8, 2002 (JP) .............................. 2002-198402
Jul. 9, 2002 (JP) .............................. 2002-199715

(51) Int. Cl.
A62B 7/08  (2006.01)
C10J 1/10  (2006.01)
B01D 25/00 (2006.01)

(52) U.S. Cl. .................. 422/121; 261/104; 261/107; 210/295; 210/296

(58) Field of Classification Search .............. 261/75, 261/119, 104, 107, DIG. 46; 210/295, 296, 210/198.1, 696, 764; 96/50, 80, 82; 422/120, 422/121; 205/701, 745
See application file for complete search history.

(56) References Cited

U.S. PATENT DOCUMENTS

| | | | | |
|---|---|---|---|---|
| 4,049,531 A | * | 9/1977 | Ban | 204/278.5 |
| 4,839,014 A | * | 6/1989 | Park et al. | 204/265 |
| 5,028,906 A | * | 7/1991 | Moriya et al. | 338/35 |
| 5,783,117 A | * | 7/1998 | Byassee et al. | 261/29 |
| 6,033,806 A | * | 3/2000 | Sugiura et al. | 429/229 |
| 6,720,576 B1 | * | 4/2004 | Nakajima et al. | 257/53 |

(Continued)

FOREIGN PATENT DOCUMENTS

JP       04-335934       11/1992

(Continued)

OTHER PUBLICATIONS

English Translation of Japanese Publication No. JP 11028326 A; Suga, Y, "Electrically opeated purifier for indoor air has pair of endless loop filters suspended between motor driven rollers which pass through electrolytic water in tank provided with electrodes" Feb. 2, 1999.*

*Primary Examiner*—Jill Warden
*Assistant Examiner*—Kevin C Joyner
(74) *Attorney, Agent, or Firm*—Panitch Schwarze Belisario & Nadel LLP

(57) ABSTRACT

The present invention provides a humidifier capable of removing microorganisms without using electric power. The humidifier includes a reservoir; a humidification system including a humidification filter arranged such that at least part thereof is immersed in water and a blowing means for discharging air through the humidification filter; and a microorganism remover including a first electrode and a second electrode having different electric potentials and opposing to each other to have a space therebetween and a short circuit part for causing a short circuit between the first and second electrodes. The first electrode is higher than the second electrode in electric potential and at least the first and second electrodes are arranged in contact with water in the reservoir.

29 Claims, 13 Drawing Sheets

U.S. PATENT DOCUMENTS

| | | | |
|---|---|---|---|
| 6,972,080 B1 * | 12/2005 | Tomioka et al. | 204/600 |
| 7,040,101 B2 * | 5/2006 | Takeda et al. | 62/78 |
| 2002/0197520 A1 * | 12/2002 | Quick et al. | 429/32 |

FOREIGN PATENT DOCUMENTS

| | | | |
|---|---|---|---|
| JP | 11028326 A * | | 2/1999 |
| JP | 11-204148 A | | 7/1999 |
| JP | 2001079067 A | | 3/2001 |
| JP | 2002-012239 A | | 1/2002 |
| JP | 2002122339 A | | 4/2002 |
| WO | WO 00/77163 A1 | | 12/2000 |

* cited by examiner

F I G. 9
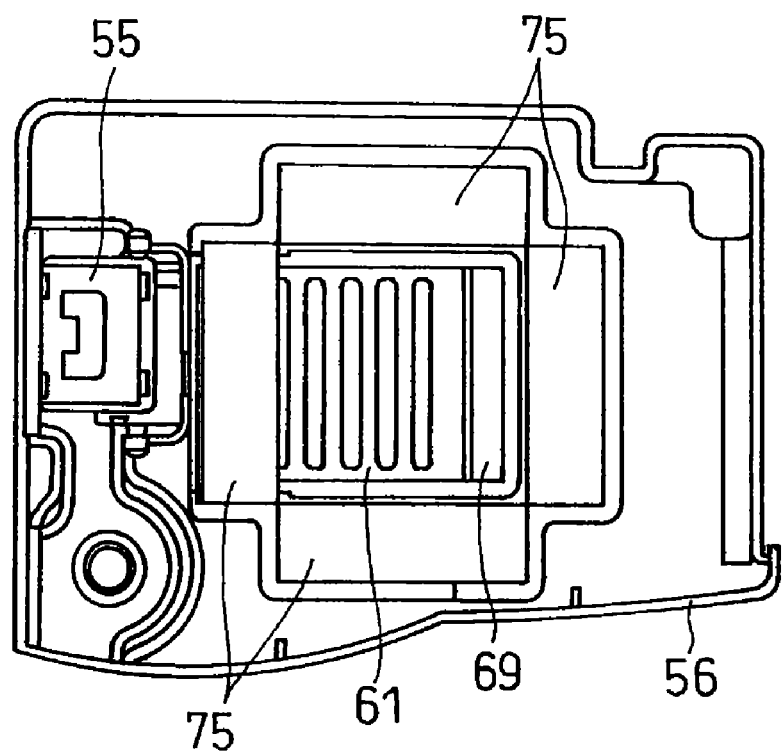

Back View

HUMIDIFIER

BACKGROUND OF THE INVENTION

The present invention relates to removal of microorganisms capable of multiplying in water retained in a humidifier (microorganism removal). More specifically, it relates to a humidifier capable of removing microorganism from water in a reservoir, sucking water after the microorganism removal into a humidification filter and discharging air humidified through the humidification filter.

In a conventional humidifier, outside air is inhaled and water in the humidifier is vaporized to discharge the inhaled air together with the vapor outside the humidifier. In the water retained in the humidifier, is observed multiplication of microorganisms such as bacteria including *E. coli* and *S. aureus*. As for an ultrasonic humidifier from which water atomized by ultrasonic waves is discharged, the microorganisms grown in the retained water may possibly be discharged alive. The humidifier also has a side effect of cooling the air.

On the other hand, a heating humidifier discharges high temperature vapor from a built-in boiler. Accordingly, even if the microorganisms are multiplied while the humidifier is out of service, they are sterilized by heat and hence the possibility of discharging the microorganisms alive is low. Such a humidifier has been designed not to discharge dead microorganisms in the air, but has a problem of high power consumption of the heater.

In contrast to these, there is a so-called hybrid humidifier in which water is sucked up to a humidification filter and air humidified through the humidification filter is discharged. However, also in this humidifier, the microorganisms are multiplied in the retained water while the humidifier is left unoperated. If the humidifier is left for an extremely long time, the multiplication of the microorganisms may be accompanied with a rot odor. On this account, there has been longed for a technique of inhibiting the microorganism multiplication in the humidifier and removing the microorganism.

For example, Japanese Laid-Open Patent Publication No. 2002-12239 proposes a hybrid humidifier as shown in FIGS. 16 to 18. FIG. 16 is a schematic perspective view of the prior art humidifier, FIG. 17 is a schematic perspective view illustrating an inner structure of the humidifier of FIG. 16 and FIG. 18 is another schematic perspective view illustrating the inner structure of the humidifier of FIG. 16.

This humidifier includes an inlet opening 100a and an outlet opening 100b opened in the main body or a cover. The main body contains therein a reservoir 102 for receiving water supplied from a water reservation tank 101, a heating tube 103 for heating water in the reservoir 102 and a water absorber 104 (humidification filter) surrounding the heating tube 103 to suck up the water in the reservoir 102. Further, an air path is formed from the inlet opening 100a through a blower 105 to the outlet opening 100b. Air introduced from the inlet opening 100a is discharged by the blower 105 together with a vapor generated from the water absorber 104 out of the outlet opening 100b. Thus, the room air is humidified.

Water in the water reservation tank 101 is supplied to the reservoir 102. The reservoir 102 includes, somewhere in the inside thereof, a pair of electrodes 107 which releases an antimicrobial substance. A degree of humidification is varied by passing electricity between the electrodes and changing the polarities at a predetermined cycle. However, in the prior art humidifier, carrying electricity to the electrodes 107 needs to be controlled to inhibit the microorganism multiplication, which complicates the humidifier and increases power consumption.

On the other hand, as a means of inhibiting the microorganism multiplication, irradiation of ultraviolet rays and intermittent heating have been proposed. However, while the humidifier is left unoperated, power supply is stopped in many cases and hence these means are relatively difficult to adopt in a practical sense. From this point of view, there is demanded for a humidifier capable of inhibiting the microorganism multiplication and disinfecting the bacteria with use of a small power generated by a storage power source, without using an external power source.

As described in Japanese Laid-Open Patent Publication No. HEI 4-335934, it is also conceivable to prevent the microorganism multiplication by adding or applying an antimicrobial substance to the components of the humidifier. In this case, however, the antimicrobial effect is insufficient because it is exerted only on the surface of the components, which results in a low degree of prevention of the microorganism multiplication in water retained or flowing in the humidifier.

International Publication WO 00/77163 A1 discloses a technique of removing protein-coated particles by moving them between the electrodes without using the external power source. This technique is considered as a solution to the problems involved with the conventional humidifiers.

BRIEF SUMMARY OF THE INVENTION

Under the above-described circumferences, an object of the present invention is to provide a humidifier capable of controlling the microorganism multiplication in internal water and eliminating bacteria with a simple structure and by a safe, highly persistent and inexpensive method using no electric power. Still another object is to provide a humidifier capable of removing living microorganisms that may possibly proliferate in internal water by a physical means.

The present invention relates to a humidifier comprising:
a reservoir;
a humidification system including a humidification filter arranged in the reservoir such that at least part thereof is immersed in water and a blowing means for discharging air humidified through the humidification filter;
a microorganism remover including a first electrode and a second electrode having different electric potentials with oxidation-reduction reaction and opposing to each other to have a space therebetween and a short circuit part for causing a short circuit between the first electrode and the second electrode,
wherein the first electrode is higher than the second electrode in electric potential and at least the first electrode and the second electrode are arranged in contact with water in the reservoir.

In the humidifier, it is preferred that the microorganism remover is arranged in the reservoir.

It is preferred that the microorganism remover is arranged in the vicinity of a water inlet of the reservoir.

It is preferred that the microorganism remover is arranged below the humidification filter.

It is preferred that the second electrode is positioned below the first electrode in a direction of gravity.

It is preferred that the short circuit part is positioned above a water surface.

It is preferred that the first and second electrodes have an electric potential difference between of 0.3 V or more.

It is preferred that the space between the electrodes is 30 mm or less.

It is preferred that the second electrode has an electric potential smaller than that of water and is made of a metal which is inert to form a protective oxide layer on its surface.

It is preferred that the second electrode is made of zinc or a zinc alloy.

It is preferred that the surface of the second electrode is phosphated.

It is preferred that the second electrode is detachable from the microorganism remover or the humidifier and surface-cleanable.

It is preferred that a contamination degree of the second electrode is visually checked.

It is preferred that the first electrode and the short circuit part are electrically connected via a first connector made of the same material as that of the first electrode and the second electrode and the short circuit part are electrically connected via a second connector made of the same material as that of the second electrode.

It is preferred that the first connector and the second connector have a clearance therebetween and the clearance is larger than the space between the first electrode and the second electrode. That is, it is preferred to provide a portion in which the first and second connectors are arranged to have a larger clearance than the space between the first and second electrodes.

It is preferred that the surfaces of the first connector and the second connector other than the short circuit part are electrically insulated and/or added with water repellency.

It is preferred that not less than 25% by volume of water retained in the reservoir exists in the space. That is, the amount of water existing in the space is 25% by volume or more of the water retained in the reservoir.

It is preferred that the microorganism remover includes a housing for accommodating the first electrode, the second electrode and the short circuit part and the housing includes a spacer for providing the space.

It is preferred that the housing is L-shaped and includes a horizontal portion for accommodating the first electrode and the second electrode while making the first and second electrodes in contact with water and a vertical portion for accommodating the short circuit part while positioning the short circuit part above a water surface.

It is preferred that the humidifier includes an installation casing for accommodating the humidification filter and the installation casing and the housing are integrated.

It is preferred that the humidifier includes a microorganism removal filter for removing microorganisms from air flown into the humidification filter.

It is preferred that the microorganism remover is detachable from the humidifier.

While the novel features of the invention are set forth particularly in the appended claims, the invention, both as to organization and content, will be better understood and appreciated, along with other objects and features thereof, from the following detailed description taken in conjunction with the drawings.

BRIEF DESCRIPTION OF THE SEVERAL VIEWS OF THE DRAWING

FIG. 9 is a top view observed in a direction of arrow Y of FIG. 8.

DETAILED DESCRIPTION OF THE INVENTION

Figure 1:
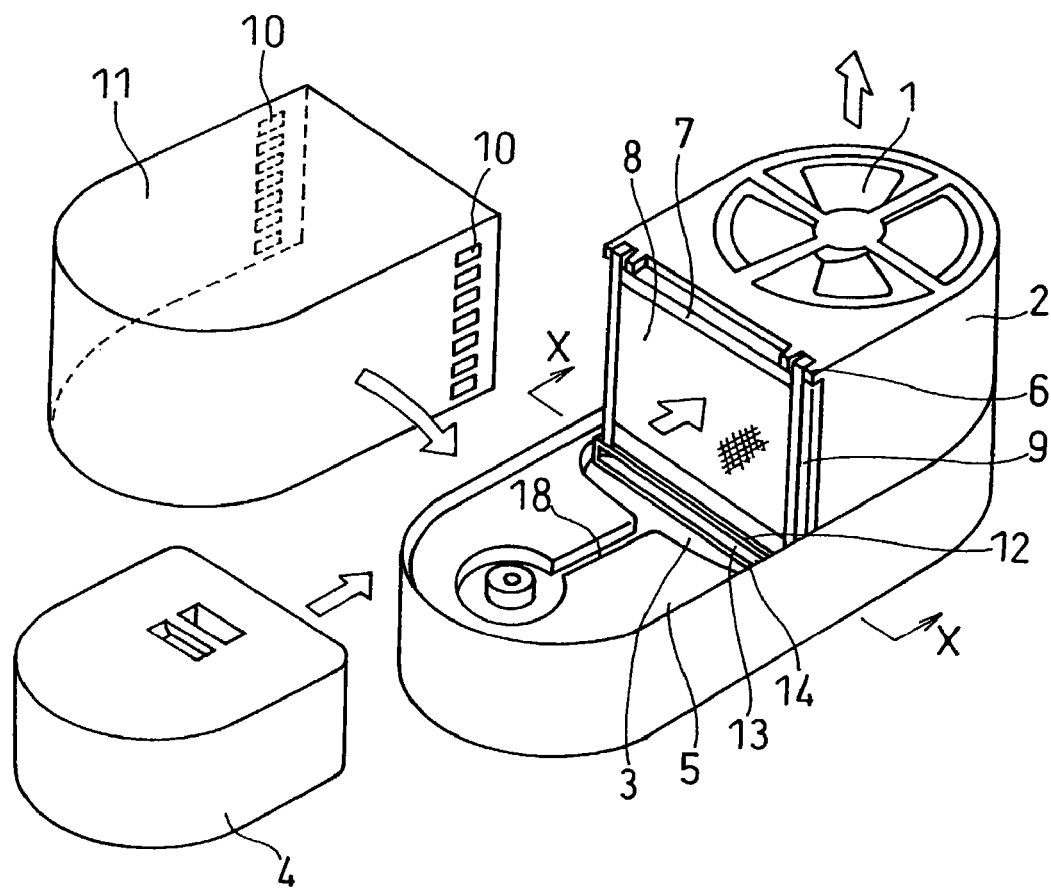
FIG. 1 is an exploded perspective view schematically illustrating a structure of a humidifier according to the present invention.

The present invention relates to a so-called hybrid humidifier for discharging air humidified through a humidification filter capable of absorbing and retaining water sucked up from a reservoir. More specifically, the present invention relates to a humidifier provided with a water supply unit including at least a water reservation tank and a reservoir, and a humidification system including a humidification filter arranged in the reservoir such that at least part thereof is immersed in water and a blowing means for discharging air humidified through the humidification filter.

The most important feature of the humidifier according to the present invention, which is a solution to the above-described problems, is that the humidifier is provided with a microorganism remover including a first electrode and a second electrode having different electric potentials with oxidation-reduction reaction (or ionization tendencies), which is hereinafter referred to as electric potential, and opposing to each other to have a space therebetween and a short circuit part for causing a short circuit between the first electrode and the second electrode, the first electrode being higher than the second electrode in electric potential and at least the first electrode and the second electrode being arranged in contact with water in the reservoir.

Accordingly, components other than the above may be the same as those of a conventional humidifier. However, in order to exert the action and effect of the microorganism remover to the maximum extent, the humidifier of the present invention is preferably configured in line with Embodiments and Examples to be described below.

First, explanation is given of the microorganism remover of the present invention.

The microorganism remover includes first and second electrodes having different electric potentials and opposing to each other to have a space therebetween with the intervention of a spacer, for example. Further, a short circuit part is provided to cause a short circuit between the first and second electrodes. Material (metal) for the first electrode is higher in electric potential than material for the second electrode.

Microorganisms that may multiply in water in the reservoir of the humidifier have a cell membrane based on protein, and therefore have a certain electric charge derived from the protein cell membrane. Paying attention to this point, the inventors of the present invention have achieved the humidifier capable of making a short circuit between the first electrode having a higher electric potential and the second electrode having a lower electric potential to move the microorganisms from the first electrode to the second electrode, thereby physically removing the microorganisms from water between the electrodes.

To the reservoir of the humidifier, almost aseptic and drinkable water such as tap water is supplied through the water reservation tank by a user. Accordingly, the amount of the microorganisms is considered extremely small in the water supplied from the water reservation tank to the reservoir. Nevertheless, water retained in the humidifier is in contact with the air and allows the migration and multiplication of the microorganisms. On this account, the microorganism remover exerts its effect in the humidifier of the present invention.

The fundamental operation principle of the microorganism remover is described below. When the first and second electrodes having different electric potentials are immersed in the retained water in the humidifier, which is an electrolyte, an electric potential difference is generated between the electrodes. At this time, if the first and second electrodes are short-circuited at one end above a water surface, the second electrode having a lower electric potential becomes an anode and the first electrode having a higher electric potential becomes a cathode. There is effected an attraction to move microorganisms from the cathode to the anode. Since the microorganisms are usually charged negative due to their cellular structure, they accumulate onto the second electrode having the lower electric potential.

When the microorganisms have accumulated onto the surface of the second electrode, they lose their multiplication capacities due to the influence of metal ions released from the second electrode surface. The microorganisms also lose their electric charges due to the electrical effect on the second electrode surface, and hence their cell membranes are destroyed. Alternatively, since the microorganisms accumulate to such a degree that space between each microorganism is extremely reduced and a usual multiplication environment cannot be made, the microorganisms cannot obtain enough oxygen or nourishment, and thereby lose their multiplication capacities to become inactive.

As the first and second electrodes, electrodes having different electric potentials may be combined. However, in order to move the microorganisms with reliability, two electrodes having an electric potential difference of 0.3 V or more are preferably used. The electric potential difference is preferably about 1.0 V.

Table 1 shows examples of metals usable for the electrodes of the present invention and their electric potentials (standard electrode electric potential E in an aqueous solution (25° C.)). The present invention is not limited thereto and alloys containing these metals are also usable.

TABLE 1

| Kind of metal | Oxidation-reduction potential (V) |
|---|---|
| Au | +1.69 |
| Pt | +1.19 |
| Ag | +0.799 |
| Cu | +0.337 |
| Pb | −0.126 |
| Ni | −0.25 |
| Sb | −0.26 |
| Co | −0.277 |
| W | −0.32 |
| Fe | −0.440 |
| Sn | −0.50 |
| Cr | −0.744 |
| Zn | −0.763 |
| V | −1.23 |
| Al | −1.66 |
| Ti | −1.72 |
| Zr | −1.95 |
| Mg | −2.27 |

Among metals indicated in Table 1, a combination of Cu (+0.337 V) and Zn (−0.763 V) is preferable because of the large electric potential difference, inexpensiveness and easy availability. The use of a zinc alloy is also preferable. However, if the electric potential difference between the electrodes is larger than an electrolysis voltage of water, it is disadvantageous because hydrogen is generated on the electrode surface, which tends to consume the electrodes to a great extent.

The microorganism removal performance of a practical level is exerted as long as the space between the first and second electrodes is 30 mm or less. Most preferably, the space is 500 µm to 6 mm. The space is preferably uniformed so that the microorganism removal effect is expected on the whole electrode surface. If the space is not uniform, the microorganism removal effect is exerted only partially on the electrode, which may decrease the microorganism removal performance as a whole.

The structure and shape of the first and second electrodes are not particularly limited as long as the effect of the humidifier of the present invention is not impaired. For example, the electrodes may be in the form of a film, a plate or a rod that allows the microorganisms to pass through. The electrodes may be made of sintered metal or may be formed by applying the metal onto an insulating base of thermoplastic resin by vapor deposition or sputtering.

In the present invention, the microorganisms are moved (migrated) from the first electrode having a higher electric potential to the second electrode having a lower electric potential. Therefore, the electrodes are preferably configured so that water is movable in the space between the first and second electrodes. The first electrode may be in the form of a membrane, a textile, a fabric, a porous body, a mesh, a brush or a gauze. The second electrode may also have these forms, but the plate form is preferable for capturing the moved microorganisms with reliability.

The above-described microorganism remover is preferably detachable from the humidifier of the present invention. It is also preferred that the first and second electrodes are detachable from the microorganism remover or the humidifier. With this structure, the electrodes contaminated can be replaced with new ones. If a transparent portion and/or an aperture is made on the side surface of the humidifier such that the electrodes in the reservoir can be seen from outside, the contamination degree of the electrodes can be checked visually, which is preferable.

Next, brief explanation is given of the humidification system of the humidifier according to the present invention.

The humidification filter is made of an electrically insulating porous body capable of absorbing and retaining water and arranged to suck up water in the reservoir. Examples of the porous body include nonwoven fabric, woven fabric, textile, interconnecting foam, paper and the like. Material for the porous body includes thermoplastic resins such as polypropylene and polyesters including polyethylene terephthalate. Synthetic fibers and natural fibers such as pulp may also be used. In view of water absorption and retention, hydrophilic material is preferably used.

For example, the humidification filter may be made of a foldable sheet having honeycomb apertures. Such a humidification filter can be folded into small size to be stored while it is not in use. In use, the filter is extended and attached to the humidifier. The humidification function is exerted by passing air through the humidification filter.

Accordingly, it is needless to say that the humidification filter is also preferably detachable from the humidifier. For example, mounting frames are attached to both ends of the humidification filter and engaging parts for detachably engaging with the mounting frames are formed in the humidifier. This structure allows easy attaching/detaching and replacing of the humidification filter.

As the blowing means in the humidifier according to the present invention, for example, an ordinary fan motor or blower may be used. Atmospheric air introduced from an inlet opening provided in the main body or a cover is humidified and then discharged by the blowing means out of an outlet opening provided in the cover, for example.

The water supply unit mainly includes a water reservation tank and a reservoir, which may be integrated as a single member or separated. The water reservation tank preferably has a means of feeding water to the reservoir such that a certain water level is maintained in the reservoir. Thus, the humidifier of the present invention offers stable humidification function with a simple structure and a low component count.

Regarding the humidifier according to the present invention, it is preferred that the microorganism remover described above is arranged below the humidification filter to deliver the physical microorganism removal function. This improves the effect of moving the microorganisms by making use of gravity in addition to the above-described electric potential difference. The microorganism multiplication in the retained water in the humidifier is inhibited by adding the microorganism removal function, thereby preventing the formation of slime and a rot odor caused by the multiplication of microorganisms in the humidification water.

Features of the humidifier of the present invention are as described above. Other components than those described above may optionally be designed by a person skilled art as long as the effect of the present invention is not impaired.

Hereinafter, the present invention is detailed by way of embodiments with reference to the drawings, but the invention is not limited thereto.

EMBODIMENT 1

FIG. 1 is an exploded perspective view schematically illustrating a structure of a humidifier according to the present invention. As shown in FIG. 1, the humidifier includes a blowing means 2 having a fan motor 1, a water reservation tank 4 for feeding water to a reservoir 3 to maintain a certain water level in the reservoir 3 and upper and lower engaging parts 6 for mounting a humidification filter 7 in the vicinity of an inlet opening (not shown) of the blowing means 2.

The humidification filter 7 is a hydrophilic sheet with honeycomb apertures made of a mixture of synthetic fiber and pulp or long fiber pulp of cotton thread and has water absorbing capacity of 150 mm/10 minutes as measured by a water absorption test of Klemm method pursuant to JIS P 8141. The hydrophilic sheet has been folded until time of use, which is extendable to form a filter unit 8. The humidification filter 7 includes on both sides thereof mounting frames 9 made of paper having water resistance and rigidity, which are engaged with the engaging parts 6 of the blowing means 2 in the main body 5, thereby providing a filter unit 8.

Figure 2:
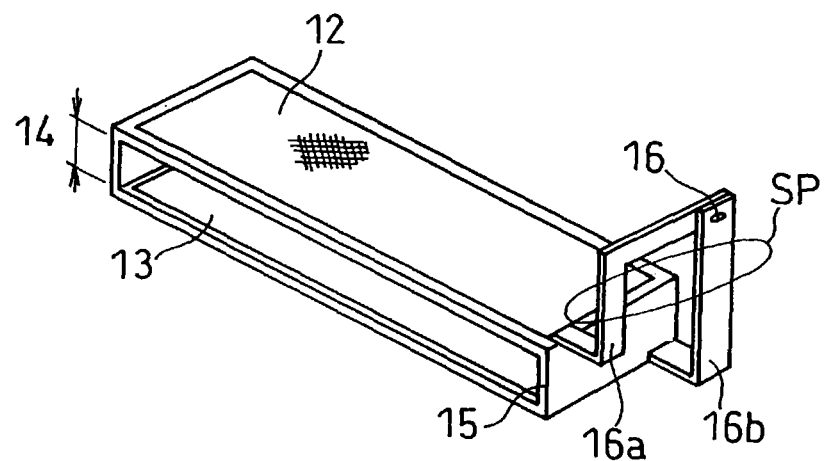
FIG. 2 is a schematic perspective view illustrating a structure of a microorganism remover adopted in Embodiment 1 of the present invention.

On the water reservation tank 4, a cover 11 provided with inlet openings 10 and an opening for supplying air to the inlet opening (not shown) of the blowing means 2 is placed. A microorganism remover is arranged below the filter unit 8. The microorganism remover includes, as shown in FIG. 2, a copper mesh 12 arranged in contact with the filter unit 8 to function as the first electrode and a zinc alloy plate 13 functions as the second electrode, which are opposing to each other to have a certain space 14 therebetween. FIG. 2 is a schematic perspective view illustrating a structure of the microorganism remover used in this embodiment. This microorganism remover is arranged below the filter unit 8 of FIG. 1.

Figure 3:
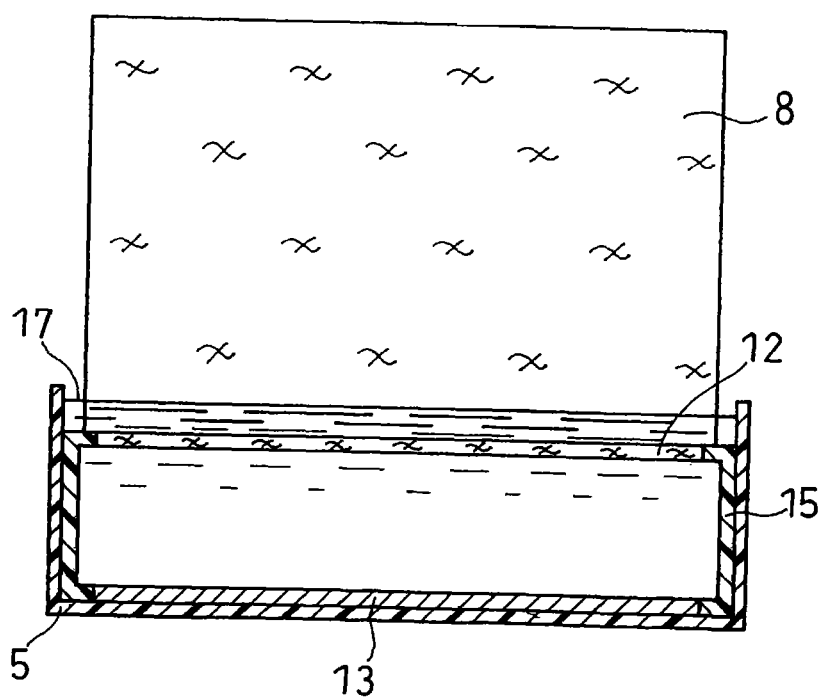
FIG. 3 is a sectional view taken along the line X-X of FIG. 1 schematically illustrating a section of the microorganism remover installed in the humidifier according to the present invention.

FIG. 3 is a sectional view taken along the line X-X of FIG. 1 schematically illustrating a section of the microorganism remover installed in the humidifier of the present invention. Referring to FIGS. 2 and 3, the copper mesh 12 and the zinc alloy plate 13 are fixed by a frame 15 to be opposed to each other in parallel to have a certain space therebetween. In order that the copper mesh 12 and the zinc alloy plate 13 function as the electrodes, respectively, connectors (leads) are attached thereto. More specifically, a first connector 16a made of a copper mesh is formed at one end of the copper mesh 12 and a second connector 16b made of a zinc alloy is formed at one end of the zinc alloy plate 13, which are electrically connected above a water surface 17 to form a short circuit part 16.

The copper mesh 12 is preferably an oxygenfreecopper mesh having a mesh of #20 and a size of 5×15 cm, which is almost the same as an area of the bottom of the filter unit 8 contacting water. The zinc alloy plate 13 is preferably made of an alloy of zinc with 0.35% of copper, 0.07% of titanium and 0.003% of aluminum. As compared with pure zinc, the zinc alloy plate is slightly higher or almost equal in electric potential and superior in corrosion resistance. The zinc alloy plate is capable of retaining its mechanical strength over the long run even if it is immersed in water for a long time.

In order to improve the corrosion resistance of the zinc alloy plate 13, it is preferable that one of the surfaces of the zinc alloy plate 13 is phosphated and the other is coated with resin (e.g., 100 to 200 μm in thickness). The size of the zinc alloy plate 13 is almost the same as that of the copper mesh 12. The phosphating surface of the zinc alloy plate 13 is faced to the copper mesh 12 and the resin-coated surface contacts closely the bottom of the reservoir 3.

These two electrodes are fixed by the frame 15 such that the electrodes are arranged in parallel with each other to have a space of 500 μm to 30 mm therebetween uniformly over the entire electrode surface other than the connectors. The first and second connectors 16a and 16b are so arranged to have a portion SP below the water surface where a clearance therebetween is made larger than the space between the electrodes so as not to generate an electric current path between the connectors in the water. Further, the connectors provide a short circuit part 16 above the water surface. Parts of the first and second connectors 16a and 16b immersed in water are made insulative by coating the parts with insulating layers using resin.

Further, in order to prevent adhesion of water to the connector surface and water absorption due to capillarity between the connectors which are brought closer to each other by forming the insulating layers, water repellent layers may be formed on the connector surfaces using fluororesin. Thus, the copper mesh 12 and the zinc alloy plate 13 which are short-circuited at a short circuit part 16 provide the microorganism remover as shown in FIG. 2. This microorganism remover is designed to be detachable from the humidifier.

The zinc alloy plate 13 dissolves to release zinc ions while the humidifier is operated, and hence zinc carbonate, zinc hydroxide or zinc oxide is deposited on the surface of the zinc alloy plate 13. In order to check the deposited compound visually from outside, it is preferred to provide an inspection window by embedding a transparent member or providing an aperture on the side surface of the humidifier. This allows a user to know when the humidifier requires maintenance.

For mounting the humidification filter 7 to the main body 5, the microorganism remover shown in FIG. 2 is arranged in the reservoir 3 and then the mounting frames 9 are engaged with the engaging parts 6 in the vicinity of the blowing means 2. Then, the humidification filter 7 which is extended is arranged above the microorganism remover such that a lower portion of the filter 7 is located below the water surface 17 in the reservoir 3.

Water in the reservoir 3 is sucked into the whole surface of the filter unit 8 by capillarity. Then, once the fan motor 1 is activated, air aspirated from the inlet opening 10 of the cover 11 passes through the filter unit 8 while vaporizing water contained in the filter unit 8, and then humidified air containing moisture is discharged from the outlet opening. When the humidification is continued to decrease the water level in the reservoir 3, the water reservation tank 4 automatically feeds water to the reservoir 3. Therefore, the reservoir 3 maintains a certain water level at any time.

Since the humidification filter 7 is made of a mixture of synthetic fiber and pulp and the mounting frames 9 are made of paper, the filter unit 8 can be incinerated after use without generating harmful substances, which is more ecologically friendly than the conventional humidifier. It is also preferable to apply an antimicrobial agent or an antifungal agent to the humidification filter 7 to prevent generation of bacteria or mold from the moisture contained in the humidification filter 7.

EMBODIMENT 2

Figure 4:
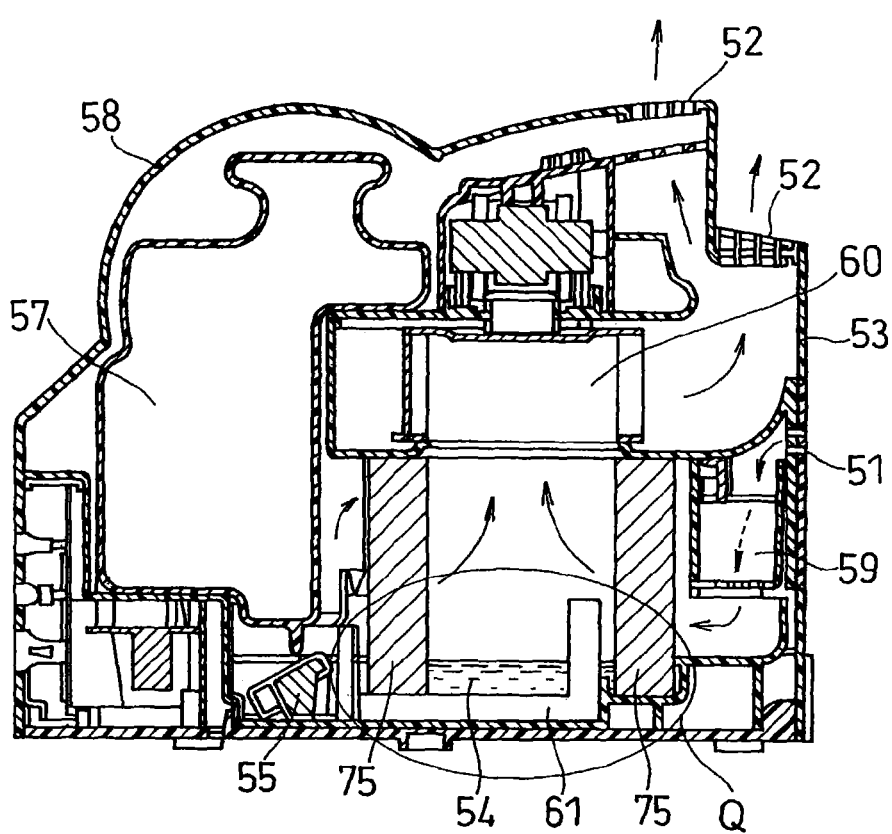
FIG. 4 is a schematic sectional view illustrating a structure of a humidifier according to Embodiment 2 of the present invention.
Figure 5:
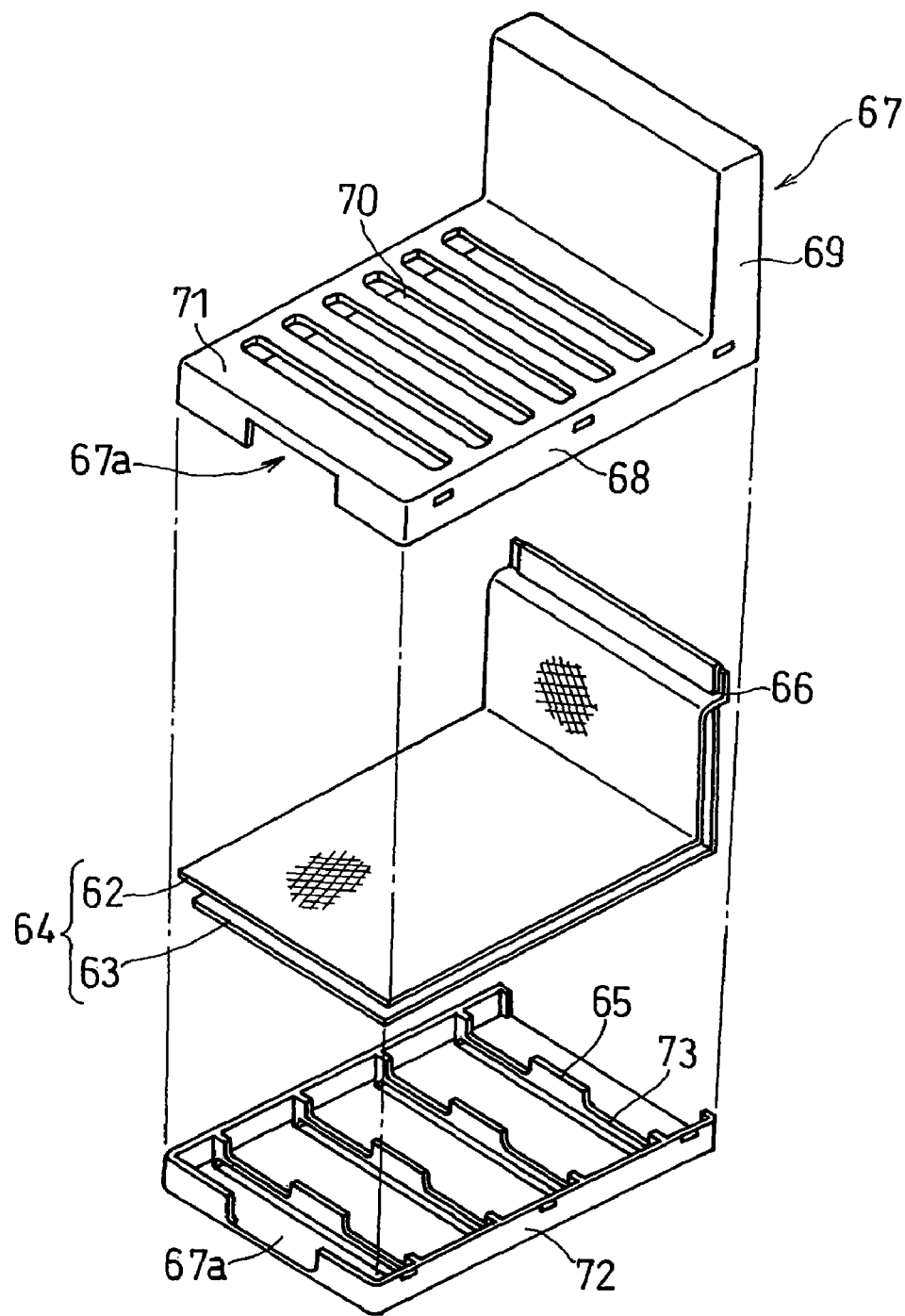
FIG. 5 is an exploded perspective view illustrating the structure of the microorganism remover according to Embodiment 2.
Figure 6:
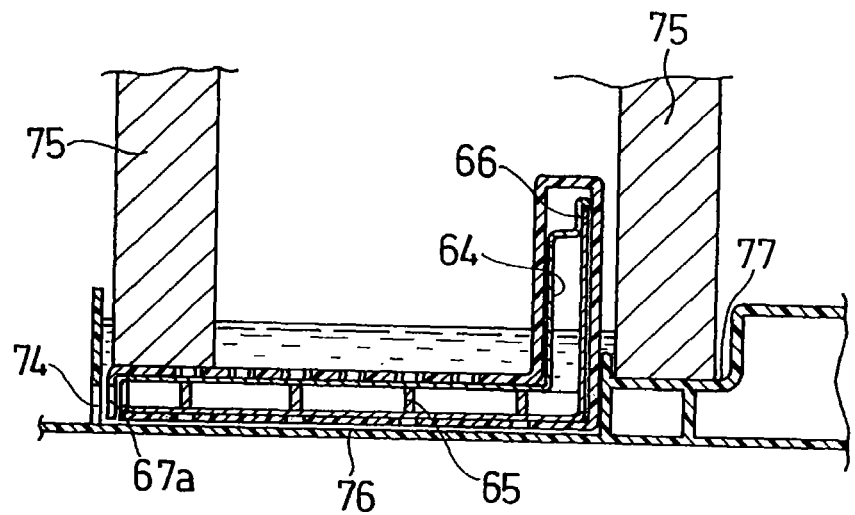
FIG. 6 is an enlarged section of part Q illustrating how the microorganism remover and the humidification filter are installed in the humidifier of FIG. 4.
Figure 7:
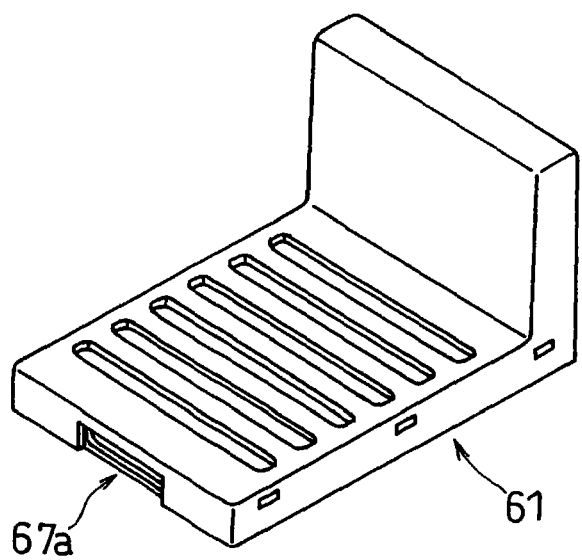
FIG. 7 is a perspective view of the microorganism remover of FIG. 5 after assembly.
Figure 8:
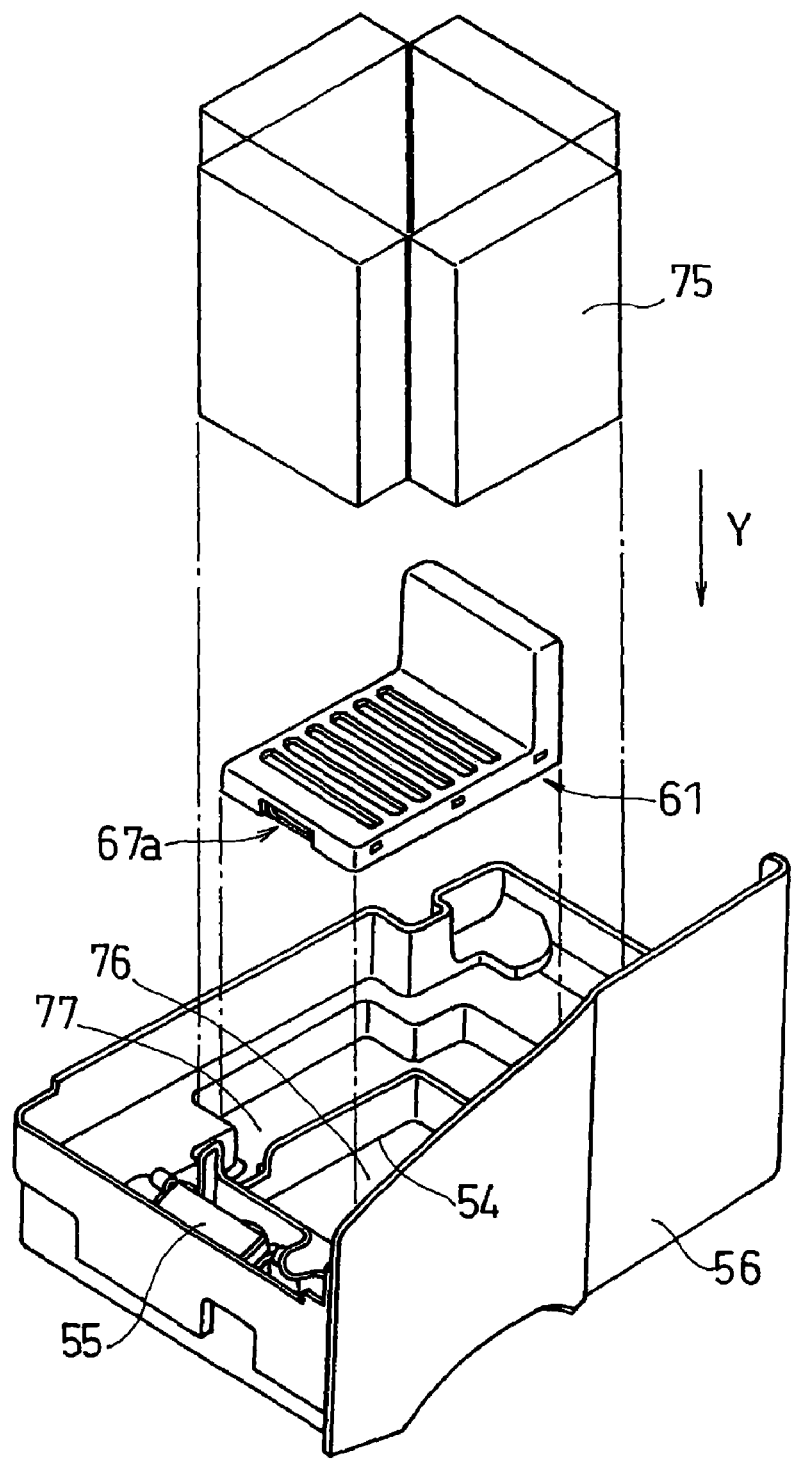
FIG. 8 is a partially cutaway view in perspective illustrating how the microorganism remover and the humidification filter are installed in a reservoir of the humidifier.

FIG. 4 is a sectional view schematically illustrating a structure of a humidifier according to Embodiment 2 of the present invention. FIG. 5 is an exploded perspective view illustrating a structure of a microorganism remover of Embodiment 2. FIG. 6 is an enlarged section of part Q illustrating how the microorganism remover and humidification filters are installed in the humidifier of FIG. 4. FIG. 7 is a perspective view of the microorganism remover of FIG. 5 after assembly. FIG. 8 is a partially cutaway view in perspective illustrating how the microorganism remover and the humidification filters are installed in a reservoir in the humidifier. FIG. 9 is a top view observed in a direction of arrow Y of FIG. 8.

As seen in FIGS. 4 to 9, a water supply unit 56 including a reservoir 54 having a level difference on the bottom and a float switch 55 for maintaining a water level is detachably installed in a lower portion of a main body 53 including an inlet opening 51 and an outlet opening 52. A water reservation tank 57 for feeding water to the reservoir 54 and a cover 58 are detachably installed in the main body 53. Further, the main body 53 includes a heater 59 for heating air aspirated from the inlet opening 51 and a blowing means 60 comprising a centrifugal fan for discharging humidified air and from an outlet opening 52.

A microorganism remover 61 placed in the reservoir 54 includes a first electrode 62 made of a copper mesh and a second electrode 63 made of a zinc plate, which are arranged horizontally to have a certain space therebetween. The first and second electrodes 62 and 63 having different electric potentials are opposed to each other with the intervention of spacers 65 which may be inserted through slits (not shown) formed in the second electrode 63. Further, the first and second electrodes 62 and 63 are connected by a short circuit part 66 formed at one end of the electrodes.

A housing 67 accommodates the first and second electrodes 62 and 63 and has an aperture 67a in the front side face. The housing 67 includes a horizontal portion 68 for accommodating the two electrodes while immersing the electrodes in water and a vertical portion 69 for accommodating the short circuit part 66 while positioning the short circuit part 66 in the air. That is, the housing 67 is almost shaped in the letter L. The housing 67 includes an upper case 71 provided with slits 70 and a lower case 72 engaging with the upper case 71. The lower case 72 includes ribs 73, with which the spacers 65 are integrated, respectively. The housing 67 may be made of an electrically insulating material such as thermoplastic resin.

The microorganism remover 61 including the housing 67 is placed in the reservoir 54 in such a manner that the aperture 67a is faced toward a water inlet 74 as shown in FIGS. 4, 6, 8 and 9. Then, a humidification filter 75 is placed surroundingly upon the microorganism remover 61. The reservoir 54 has a level difference on the bottom so that a surface 76 bearing the microorganism remover 61 is positioned lower than a surface 77 bearing the humidification filter 75.

In the thus configured microorganism remover 61, as described above, the microorganisms carry electric charges on their surfaces and move depending on an electric field. Water is fed from the water reservation tank 57 via a known water supply means through the water inlet 74 into the reservoir 54, and introduced into the microorganism remover 61 through the aperture 67a of the housing 67. Between two electrodes of the microorganism remover 61, the negatively charged microorganisms existing in water are gathered from the vicinity of the first electrode 62 made of a copper mesh having a higher electric potential to the surface of the second electrode 63 made of a zinc plate having a lower electric potential. Then, water thus sterilized is sucked into the humidification filter 75 by capillarity and retained in the humidification filter 75.

When the humidifier is activated with the water retained in the filters, room air is aspirated from the inlet opening 51 by the blowing means 60 and warmed by the heater 59. The warmed air contacts the humidification filter 75 containing water to vaporize the water. Then, the air containing vaporized water is discharged from the outlet opening 52, thereby humidifying the room with the microorganism-removed water.

In order to wash the microorganism remover 61 which has been contaminated by the microorganisms, the water reservation tank 57 is taken out at first, the water supply unit 56 is detached from the main body 53, and then the humidifier filter 75 are removed. Thereafter, the housing 67 accommodating the microorganism remover 61 is taken out of the reservoir 54 by lifting the vertical portion 69, which is then washed.

Thus, according to the humidifier of the present invention, there is no need of utilizing a complex control device for activating the microorganism remover 61. Accordingly, the structure is simplified and power saving is achieved. Further, since the microorganisms in the reservoir 54 are eliminated, the microorganism multiplication is inhibited and the formation of slime and a rot odor in the retained water is alleviated.

Since the microorganism remover 61 is arranged in the vicinity of the water inlet 74 of the reservoir 54 and the sterilized water is sucked into the humidification filter 75, water fed by the water reservation tank 57, which may contain the microorganisms, flows into the reservoir 54 through the water inlet 74 and passes through the microorganism remover 61 without fail. Therefore, humidification is performed with the microorganism-removed water.

In the microorganism remover 61, the spacers 65 for providing a space between the electrodes are integrated with the housing 67. This eliminates the need of forming the spacers separately, reducing a component count. Further, the space between the electrodes is uniformed and the microorganism remover 61 which has collected the microorganisms is washed easily.

The housing 67 is L-shaped and includes the horizontal portion 68 and the vertical portion 69. Therefore, the short circuit part 66 is avoided from submerging in water or getting wet, and hence the reduction of the microorganism removal performance is prevented. Further, the vertical portion 69 is used as a handle for attaching and detaching the microorganism remover 61 and the short circuit part 66 is protected not to come off or get damaged during the attaching and detaching.

Since the reservoir 54 has a level difference on the bottom to arrange the surface 76 bearing the microorganism remover 61 at a lower level than the surface 77 bearing the humidification filter 75, the microorganism remover 61 is positioned on the very bottom of the reservoir 54, which is inevitably submerged in water and exerts its function to a sufficient extent. Further, the bottom area of the reservoir 54 is effectively utilized to downsize the humidifier.

EMBODIMENT 3

Figure 10:
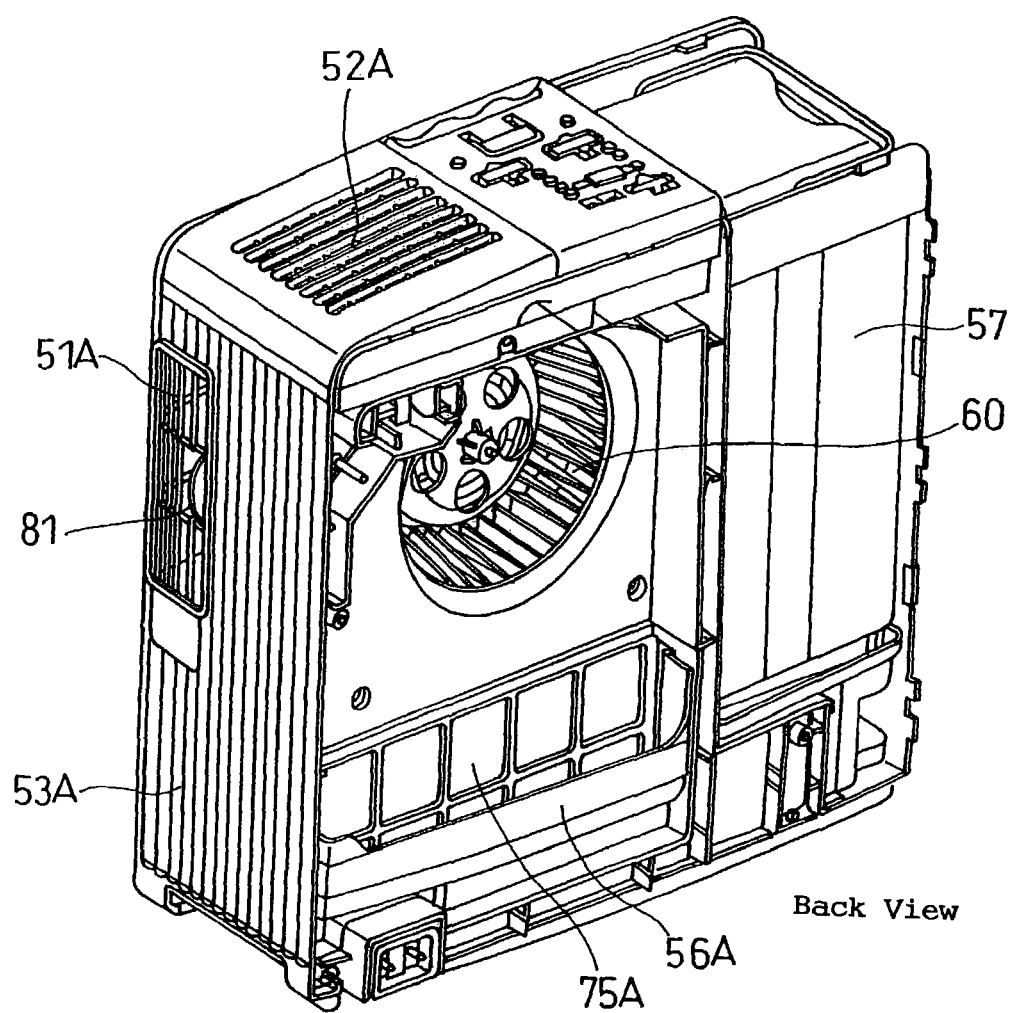
FIG. 10 is a back view in perspective illustrating the inside of a humidifier according to Embodiment 3.
Figure 11:
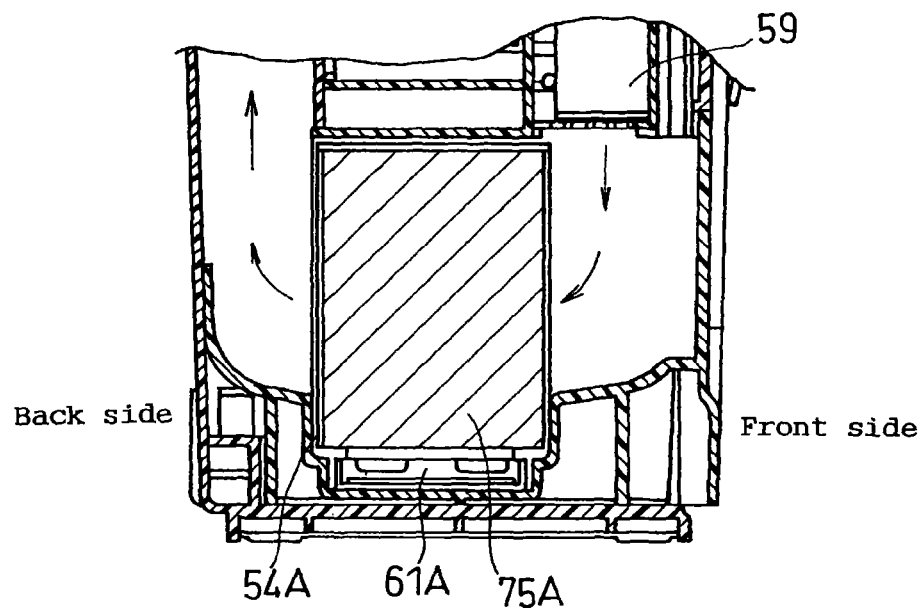
FIG. 11 is a sectional view of a major part of the humidifier of FIG. 10.
Figure 12:
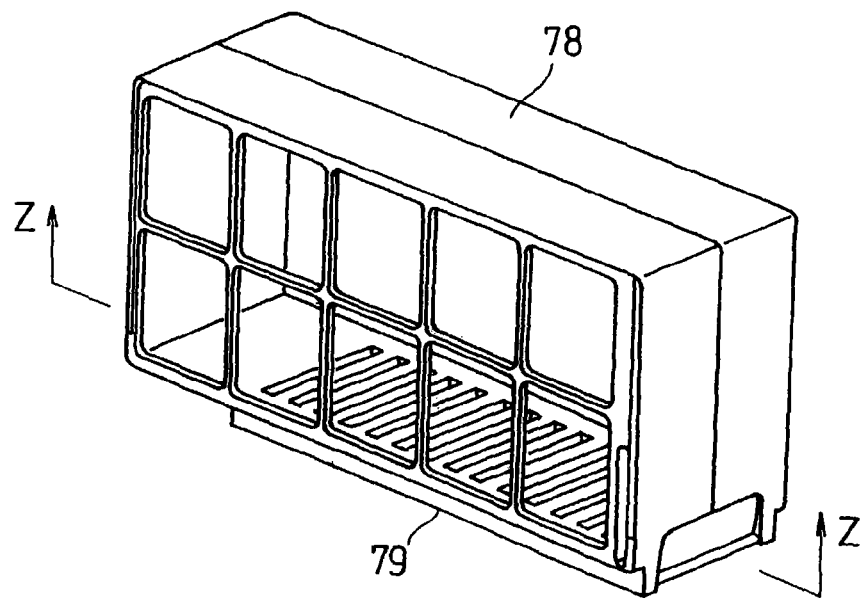
FIG. 12 is a perspective view of an installation casing for installing a humidification filter in the humidifier.
Figure 13:
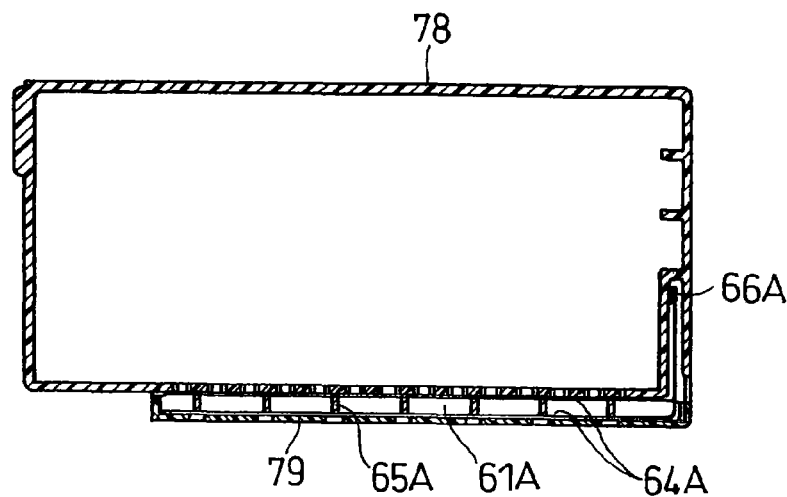
FIG. 13 is a sectional view taken along the line Z-Z shown in FIG. 12.
Figure 14:
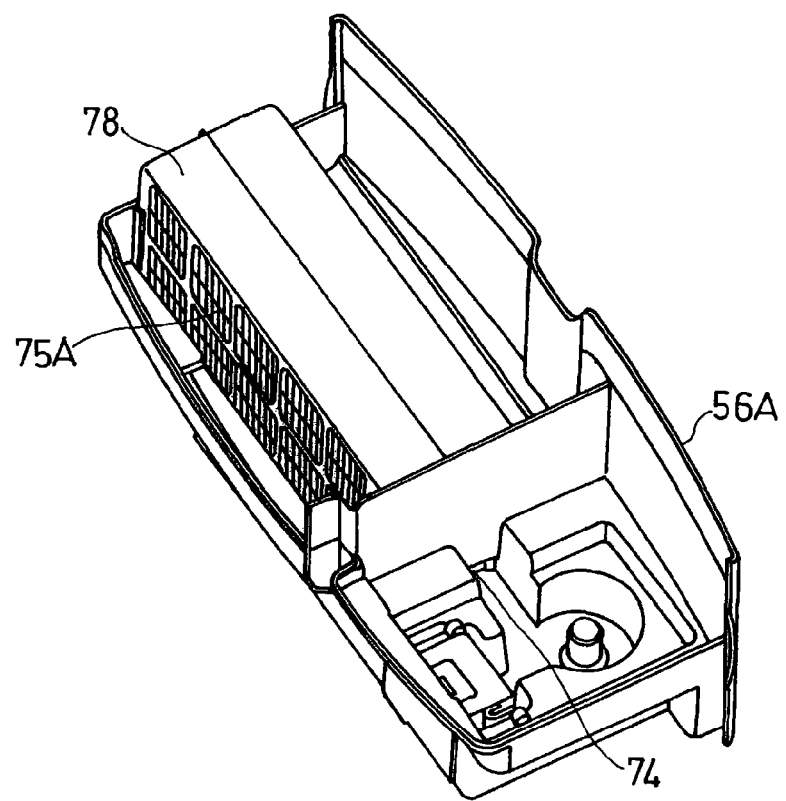
FIG. 14 is a perspective view illustrating a water supply unit in the humidifier of FIG. 10.
Figure 15:
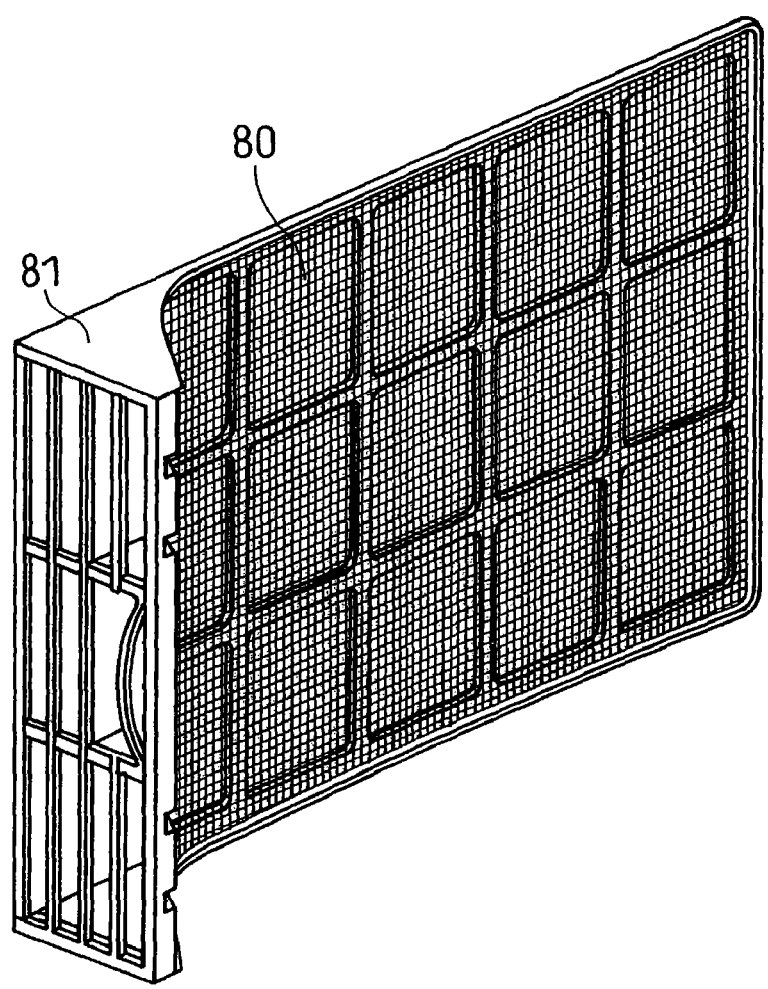
FIG. 15 is a perspective view of a microorganism removal filter.
Figure 16:
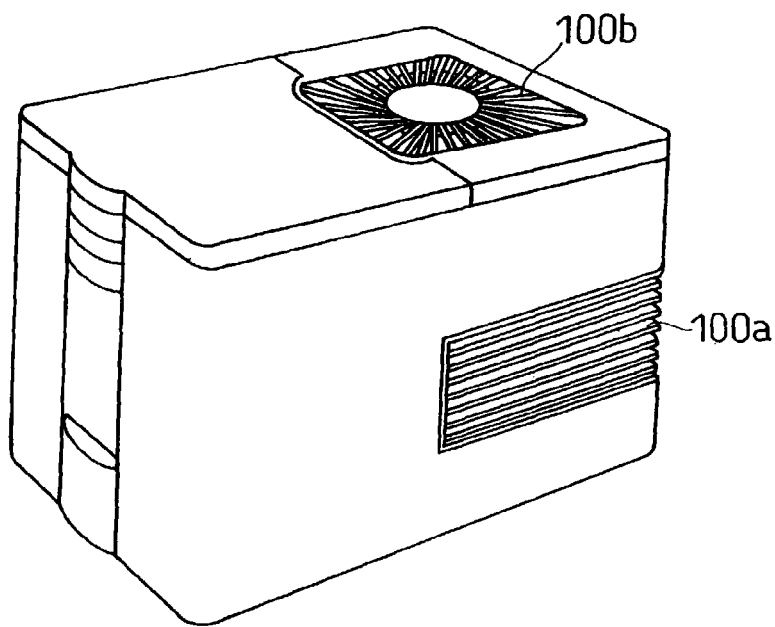
FIG. 16 is a schematic perspective view of a conventional humidifier.
Figure 17:
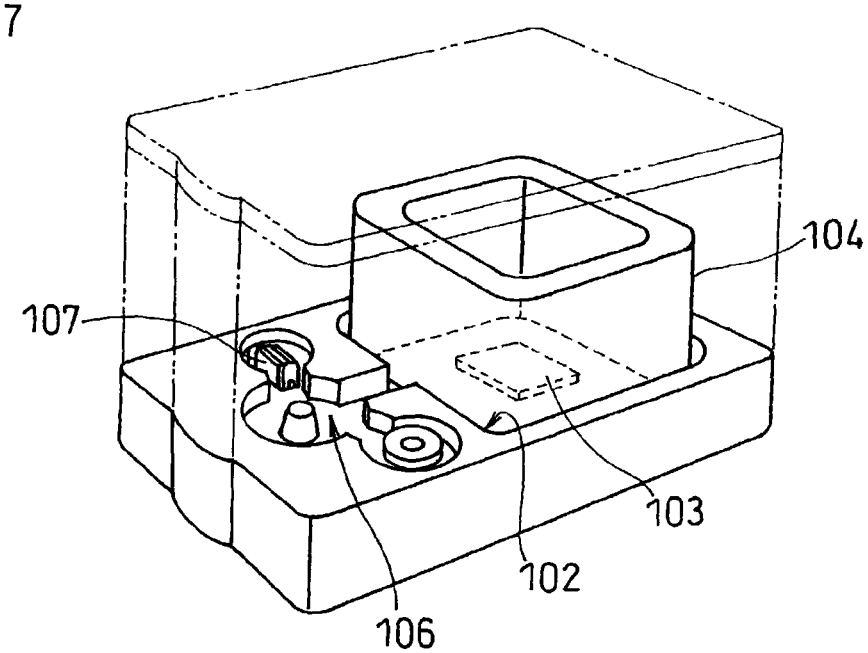
FIG. 17 is a schematic sectional view illustrating an inner structure of the humidifier of FIG. 16.
Figure 18:
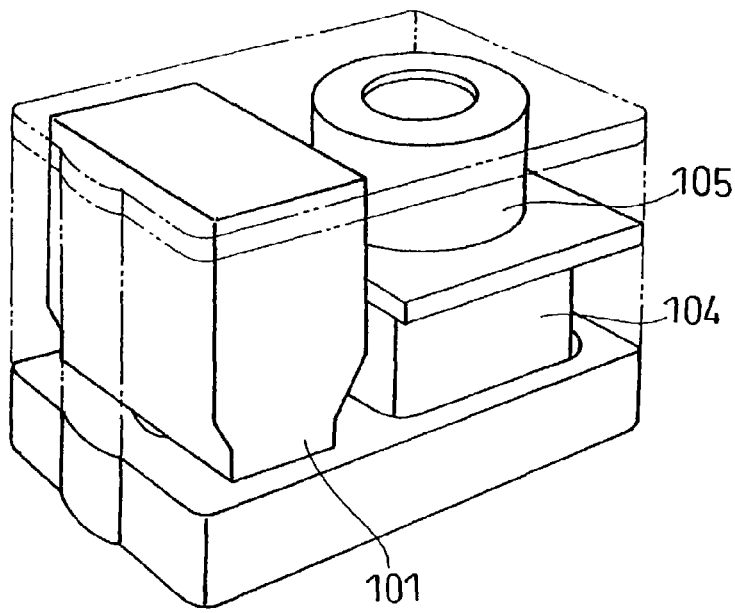
FIG. 18 is another schematic sectional view illustrating the internal structure of the humidifier of FIG. 16.

FIG. 10 is a back view in perspective illustrating the inside of a humidifier according to Embodiment 3. FIG. 11 is a sectional view of a major part of the humidifier of FIG. 10. FIG. 12 is a perspective view of an installation casing for installing a humidification filter in the humidifier. FIG. 13 is a sectional view taken along the line Z-Z shown in FIG. 12. FIG. 14 is a perspective view illustrating a water supply unit in the humidifier of FIG. 10. Further, FIG. 15 is a perspective view of a microorganism removal filter.

As shown in FIGS. 10 to 15, a water supply unit 56A is detachably installed in a main body 53A provided with an inlet opening 51A and an outlet opening 52A. A humidification filter 75A arranged in a reservoir 54A of the water supply unit 56A has an almost rectangular shape. An installation casing 78 for containing the humidification filter 75A includes a housing 79 integrated into a lower portion thereof to accommodate therein a microorganism remover 61A. In the same manner as in Embodiment 2, the microorganism remover 61A includes a pair of electrodes 64A opposing to each other with the intervention of spacers 65A and a short circuit part 66A.

To the inlet opening 51A, a detachable mounting frame 81 for mounting a microorganism removal filter 80 is preferably attached. The microorganism removal filter 80 to be mounted on the frame 81 is added with an enzyme capable of steriling bacteria suspending in the air and Ag-apatite so that the microorganisms are removed from the air flowing into the humidification filter 75A.

In the thus configured humidifier, water is fed from the water reservation tank 57 to the reservoir 54A of the water supply unit 56A installed in the main body 53A. Then, the microorganism remover 61a accommodated in the housing 79 positioned below the humidification filter 75A installed in the casing 78 and a lower portion of the humidifier 75A are submerged in the water.

When the humidifier is activated in this state, room air is aspirated by a blowing means 60 through the inlet opening 51A. Since the microorganism removal filter 80 is arranged in the inlet opening 51A, clean air from which the microorganisms are removed is warmed by a heater 59. The warmed air contacts the humidification filter 75A to vaporize water microorganism-removed by the microorganism remover 61A. Thus, humidification is performed.

According to the humidifier of Embodiment 3, the housing 79 for accommodating the microorganism remover 61A is integrated with the installation casing 78. Thereby, a distance between the humidification filter 75A and the microorganism remover 61a is kept constant at any time, and hence the antimicrobial action is stabilized and the component count is reduced. Further, since the humidification filter 75A and the microorganism remover 61A are held in the same casing, they are easily attached and detached to and from the reservoir 54A and are washed at the same time.

EMBODIMENT 4

Different from Embodiments above, a microorganism remover in a humidifier according to Embodiment 4 of the present invention includes a first electrode and a second electrode opposing to each other to have a space therebetween and an application means for applying a voltage which is lower than a voltage for initiating electrolysis of water between the first and second electrodes. In this case, the electric potential of the first electrode may not be higher than that of the second electrode as long as the first and second electrodes are arranged at least in contact with water.

It is preferred that the first electrode is positioned in the vicinity of the humidification filter and the application means applies a lower voltage to the first electrode than to the second electrode. More specifically, in the humidifier configured in Embodiment 1, a copper plate is used in place of the zinc alloy plate used as the second electrode 13, and the first electrode made of a copper mesh and the second electrode made of the copper plate are connected to a negative electrode and a positive electrode of the application means such as an external power source, respectively, instead of short-circuiting the electrodes.

The external power source is one of the components of the microorganism remover, which may be installed in the microorganism remover or the humidifier. The external power source is preferably a low voltage storage power source which is charged while the humidifier is at work. Not only in a working state but also in an out-of-service state of the humidifier, it is preferred to apply a voltage of about 0.7 V between the electrodes as long as the discharge is permitted. This voltage preferably corresponds to the above-described electric potential difference.

EMBODIMENT 5

Different from Embodiments above, a microorganism remover in a humidifier of Embodiment 5 of the present invention has an electric potential lower than the electric potential of electrolysis of water and includes an electrode made of a metal which is inert to form a protective oxide layer on its surface. The electrode is arranged at least partially in contact with water.

More specifically, in the humidifier configured in Embodiment 1, the second electrode 13 made of a zinc alloy plate is utilized as it is and the first electrode 12 made of a copper mesh is omitted. The second electrode 13 is arranged in the same manner as Embodiment 1 so that the connector 16a is positioned above the water surface to freely contact with the air. A three phase region among the zinc alloy, water and air functions as a third electrode which is linear.

In this case, a distance between the surface of the second electrode 13 and the lower end of the filter unit 8 arranged above the second electrode 13 is reduced as much as possible to exert the microorganism removal effect to a greater extent. Metal for forming the electrode preferably has an electric potential lower than that of water and is less apt to form a protective oxide film on its surface.

In Embodiments described above, a particular combination of the components other than the microorganism remover is explained. In the present invention, however, the components in each Embodiment may be combined as appropriate within the scope of the present invention. Specific examples of the present invention will be described below.

EXAMPLE 1

The humidifier according to Embodiment 1 configured as shown in FIGS. 1 to 3 was manufactured and operated to confirm the microorganism removal effect. In the water reservation tank 4 for feeding water to the reservoir 3 while maintaining a certain water level, tap water was poured. The water reservation tank 4 was configured to be detachable to allow the tank to be washed after each use.

The water poured in the water reservation tank 4 was stored in the reservoir 3 via a water path 18. Since the microorganism remover as described in Embodiment 1 was placed in the reservoir 3, the water was introduced into the microorganism remover 3. The water was sterilized and absorbed into the filter unit 8 arranged above the microorganism remover via the copper mesh 12 and vaporized by heating air blown to the filter unit 8. Then, vapor thus generated was discharged outside the humidifier.

In order to blow hot air to the filter unit 8, a heater was provided though which is not shown. The copper mesh 12 functions as the first electrode and the zinc alloy plate 13 functions as the second electrode were arranged to have a space of 6 mm. The electrodes had an electric potential difference of 0.5 V.

Microorganisms floating in the air introduced from the outside of the humidifier were blown to the filter unit 8 by the hot air and captured on the surface of the filter unit 8. Since the filter unit 8 was immersed in water in the reservoir 3 at the lower portion, some of the microorganisms captured by the humidification filter 7 were fallen due to undulation of the water surface or the like and dispersed in water. The microorganisms that had not been influenced by the antimicrobial humidification filter 7 were dispersed alive in the water. In the case where the microorganism remover was absent, such microorganisms multiplied in the water by taking nourishment from organic substances collected from the air. When left standing, the microorganisms multiplied and caused a rot odor and slime in the water.

As opposed to the above-described case, in this example, the microorganism remover was arranged in a position where the microorganisms start dispersing in the water. Therefore, the microorganisms dispersed in the water were accumulated on the surface of the second electrode 13 made of the zinc alloy plate according to the above-described principle of the microorganism removal, and then became inert. Owing to this action, the microorganism multiplication was inhibited in the reservoir 3 or surrounding water-retaining regions. Thus, the rot odor and the water slime caused by the microorganism multiplication were prevented.

EXAMPLE 2

The humidifier according to Embodiment 1 was manufactured in the same manner as Example 1. A water content between the first electrode 12 and the second electrode 13 of the microorganism remover, i.e., a retained water content P in the space between the first and second electrodes 12 and 13, was calculated. Then, was also calculated a total water amount Q in the water supplying portion except the water reservation tank 4, i.e., in the water path extending from a lower portion from the water reservation tank to the reservoir 3 and in the reservoir 3 containing the microorganism remover, above which the filter unit was arranged.

Figure 19:
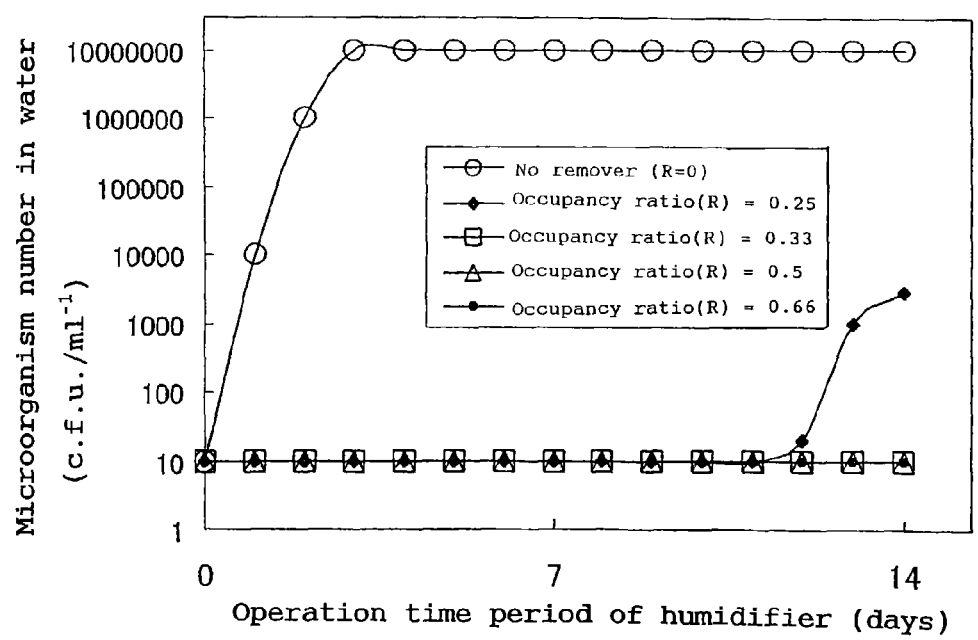
FIG. 19 is a graph illustrating a relationship between occupancy ratios R and microorganism removal performance of the humidifier of Embodiment 2.

The ratio of the retained water content P to the total water amount Q was determined as the occupancy ratio R (R=P/Q) of the retained water. FIG. 19 shows a relationship between the microorganism removal performance and the occupancy ratios R established as 0.25, 0.33, 0.5 and 0.66 by varying the volume of the reservoir 3 and the space between the electrodes of the microorganism remover. The vertical axis shows the number of microorganisms in water (c.f.u. (colony formation unit)/ml$^{-1}$). The horizontal axis shows operation time period of humidifier (days). The microorganism removal performance was measured by counting the microorganisms existing in the water in the humidifier. The microorganism removal performance of the humidifier in the absence of the microorganism remover (R=0) was also measured.

More specifically, humidifiers in which the occupancy ratios R were set to 0, 0.25, 0.33, 0.5 and 0.66, respectively, were operated at room temperature for 8 hours. After a pause of 16 hours, retained water in the microorganism remover was collected before feeding water for re-operation. The microorganisms existing in the water was counted. Each humidifier was the one for domestic use capable of vaporizing 4 liters of water for 8-hour operation, in which the microorganism remover had the size of 5×15 cm and the space between the electrodes of 6 mm.

The microorganisms (bacteria) were counted after cultured in a Nutrient agar (culture medium obtained from 5 g of meat extract, 10 g of peptone, 5 g of sodium chloride and 15 g of agar dissolved in 1 liter of pure water and sterilized; a product of NISSUI PHARMACEUTICAL CO., LTD.) at 30° C. for 48 hours by an agar plate culture method.

The microorganism removal action was judged as effective when the bacteria count was reduced to 1/100 or smaller as compared with the case where the microorganism remover was not used. If the water in the water reservation tank 4 is supposed to be replaced almost every two weeks, it is understood that the humidifier in which the occupancy ratio R is set to 0.25 or more exerts effective microorganism removal performance. With respect to the metal forming the electrodes, it is sufficient that the electric potential thereof is lower than that of water. Actually, the electrodes having the electric potential difference of 0.3 V or more showed practical microorganism removal performance.

EXAMPLE 3

In this example, a humidifier was manufactured in the same manner as Example 1 except that a microorganism remover including first and second electrodes opposing to each other to have a space therebetween and an application means for applying a voltage lower than a voltage for electrolysis of water between the first and second electrodes. The obtained humidifier was subjected to the same evaluations as those of Example 1. More specifically, a copper plate was used in place of the zinc alloy plate as the second electrode 13, and the first electrode made of a copper mesh and the second electrode made of the copper plate were connected to a negative pole and a positive pole of an external power source, respectively, in spite of short-circuiting the electrodes.

As the external power source, a low voltage storage power source charged while operating the humidifier was used. Not only in a working state but also in an out-of-service state of the humidifier, a voltage of about 0.7 V was applied between the electrodes as long as the discharge was permitted.

After operating the humidifier, it was confirmed that the humidifier of this example also exerted practical microorganism removal performance as that of Example 1.

As described above, the microorganism remover in the humidifier of the present invention has the specific structure. Accordingly, there is no need of controlling the operation of the microorganism remover by connecting an external power source, and hence power consumption is lowered. Further, since the microorganism multiplication is inhibited by the simple structure, the generation of slime and a four odor is also prevented.

Further, the microorganism remover is arranged in the vicinity of the water inlet of the reservoir so that water supplied from the water reservation tank inevitably passes through the microorganism remover. Therefore, the microorganism removal is performed with efficiency.

The microorganism remover of the present invention includes two different electrodes having different electric potentials, a short circuit part and a housing for accommodating them as required, and a space is made between the electrodes by the spacers integrated with the housing. Therefore, the component count is reduced. Further, the microorganism removal action is exerted with stability and the housing is easily taken out of the reservoir to be washed with water with ease.

The housing is configured in the form of the letter L by combining a horizontal portion for accommodating the two electrodes while immersing the electrodes in water and a vertical portion for accommodating the short circuit part while making the short circuit part contact with the air. Therefore, the short circuit part is prevented from getting wet. Further, the vertical portion is utilized as a handle for detaching the microorganism remover and the short circuit part is protected not to come off or get damaged during the detaching.

The reservoir has a level difference on the bottom so that a surface bearing the microorganism remover is positioned lower than a surface bearing the humidification filter. Accordingly, the bottom area of the reservoir is effectively used for downsizing the humidifier.

With the use of an installation casing for accommodating the humidification filter, to which a housing for accommodating the microorganism remover is integrated, the component count is reduced. Further, a distance between the humidification filter and the microorganism remover is kept constant, thereby the microorganism removal action is exerted with stability. Moreover, the humidification filter and the two electrodes can be washed at the same time.

Further, with the use of a microorganism removal filter for removing the bacteria from the air to be flown through the humidification filter, the microorganism removal is performed not only in the water in the reservoir but also in the aspirated air. Accordingly, bacteria contacting the humidification filter in the water and the air are reduced to inhibit the bacteria multiplication, which maintains sanitary conditions even in a long-term operation.

Thus, according to the humidifier of the present invention, the microorganisms migrated in the humidification water are effectively eliminated without using any agents such as an antimicrobial agent. Further, the generation of a rot odor and slime due to the migration and multiplication of the microorganisms is prevented. Therefore, the present invention is effective in improving sanitary conditions in the humidifier used to improve a living environment for promotion of health.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

The invention claimed is:

1. A humidifier comprising:
   a water source connected to a reservoir having a water inlet for supplying water thereto;
   a humidification system including a humidification filter arranged in said reservoir such that at least part thereof is immersed in water and a blowing means for discharging air humidified through said humidification filter, said humidification filter including a first part and a second part;
   a microorganism remover including a first electrode and a second electrode having different oxidation-reduction potentials and opposing to each other to have a space therebetween and a short circuit part for causing a short circuit between said first electrode and said second electrode,
   wherein said first electrode comprises a material having a higher oxidation-reduction potential than a material comprising the second electrode and at least said first electrode and said second electrode are arranged in contact with the water in which said humidification filter is immersed in said reservoir, and
   wherein said microorganism remover constitutes at least part of a passage that passes water entering said reservoir to said humidification filter such that the only water that is supplied to said second part of said humidification filter is the water that passes through said space between said first and second electrodes of said microorganism remover.

2. The humidifier in accordance with claim 1, wherein said microorganism remover is arranged in said reservoir.

3. The humidifier in accordance with claim 2, wherein not less than 25% by volume of water retained in said reservoir exists in said space.

4. The humidifier in accordance with claim 1, wherein said microorganism remover is arranged below said humidification filter.

5. The humidifier in accordance with claim 1, wherein said second electrode is positioned below said first electrode.

6. The humidifier in accordance with claim 1, wherein said short circuit part is positioned above a water surface.

7. The humidifier in accordance with claim 1, wherein said first electrode and said second electrode have an oxidation-reduction potential difference of 0.3 V or more.

8. The humidifier in accordance with claim 1, wherein said space is 30 mm or less.

9. The humidifier in accordance with claim 1, wherein said second electrode comprises a material having an oxidation-reduction potential smaller than that of water and is made of a metal which is inert to form a protective oxide layer on its surface.

10. The humidifier in accordance with claim 9, wherein said second electrode is made of zinc or a zinc alloy.

11. The humidifier in accordance with claim 10, wherein a surface of said second electrode is phosphated.

12. The humidifier in accordance with claim 1, wherein said second electrode is detachable from said microorganism remover or said humidifier and surface-cleanable.

13. The humidifier in accordance with claim 1, further comprising means for visually checking a contamination degree of said second electrode.

14. The humidifier in accordance with claim 1, wherein said first electrode and said short circuit part are electrically connected via a first connector made of the same material as that of said first electrode and wherein said second electrode and said short circuit part are electrically connected via a second connector made of the same material as that of said second electrode.

15. The humidifier in accordance with claim 14, wherein said first connector and said second connector have a clearance therebetween which is larger than the space between said first electrode and said second electrode.

16. The humidifier in accordance with claim 14, wherein surfaces of said first connector and said second connector other than said short circuit part are electrically insulated.

17. The humidifier in accordance with claim 14, wherein said first connector and said second connector have water repellency.

18. The humidifier in accordance with claim 1, wherein said microorganism remover includes a housing for accommodating said first electrode, said second electrode and said short circuit part.

19. The humidifier in accordance with claim 18, wherein said housing includes a spacer for providing said space.

20. The humidifier in accordance with claim 18, wherein said housing is L-shaped and includes a horizontal portion for accommodating said first electrode and said second electrode and retaining said first and second electrodes in contact with water and a vertical portion for accommodating said short circuit part while positioning said short circuit part above a water surface.

21. The humidifier in accordance with claim 18 further comprising an installation casing for accommodating said humidification filter, wherein said installation casing and said housing are integrated.

22. The humidifier in accordance with claim 18, wherein said housing has two or more apertures and at least one of the two or more apertures faces said water inlet of said reservoir.

23. The humidifier in accordance with claim 1 further comprising a microorganism removal filter for eliminating bacteria from air flown into said humidification filter.

24. The humidifier in accordance with claim 1, wherein said microorganism remover is detachable from said humidifier.

25. The humidifier in accordance with claim 1, wherein said short circuit part forms a constant short circuit between said first electrode and said second electrode.

26. A humidifier comprising:
a main body;
a reservoir formed in said main body having a water inlet for supplying water thereto;
a water reservation tank proximate said water inlet for feeding water to said reservoir;
a cover removably attachable to said main body, said cover and main body enclosing said water reservation tank in an operating configuration;
a humidification system including a humidification filter arranged in said reservoir such that at least part thereof is immersed in water and a blowing means for discharging air humidified through said humidification filter, said humidification filter including a first part and a second part;
a microorganism remover including a first electrode and a second electrode having different oxidation-reduction potentials and opposing to each other to have a space therebetween and a short circuit part for causing a short circuit between said first electrode and said second electrode, wherein said microorganism remover constitutes at least part of a passage that passes water entering said reservoir to said humidification filter such that the only water that is supplied to said second part of said humidification filter is the water that passes through said space between said first and second electrodes of said microorganism remover; and
wherein said first electrode comprises a material having a higher oxidation-reduction potential than a material comprising the second electrode and at least said first electrode and said second electrode are arranged in contact with the water in said reservoir.

27. A humidifier comprising:
a water source connected to a reservoir;
a humidification system including a humidification filter arranged in said reservoir such that at least part thereof is immersed in water and a blowing means for discharging air humidified through said humidification filter, said humidification filter including a first part and a second part;
a microorganism remover including a first electrode and a second electrode having different oxidation-reduction potentials and opposing to each other to have a space therebetween and a short circuit part for causing a short circuit between said first electrode and said second electrode, wherein said microorganism remover constitutes at least part of a passage that passes water entering said reservoir to said humidification filter such that the only water that is supplied to said second part of said humidification filter is the water that passes through said space between said first and second electrodes of said microorganism remover; and
wherein said first electrode comprises a material having a higher oxidation-reduction potential than a material comprising the second electrode and at least said first electrode and said second electrode are arranged in contact with the water in said reservoir.

28. A humidifier comprising:

a water source connected to a reservoir;

a humidification system including a humidification filter arranged in said reservoir such that at least part thereof is immersed in water and a blowing means for discharging air humidified through said humidification filter, said humidification filter including a first part and a second part;

a microorganism remover including a first electrode and a second electrode having different oxidation-reduction potentials and opposing to each other to have a space therebetween and a short circuit part for causing a short circuit between said first electrode and said second electrode, wherein said second electrode is positioned below said first electrode, wherein said microorganism remover constitutes at least part of a passage that passes water entering said reservoir to said humidification filter such that the only water that is supplied to said second part of said humidification filter is the water that passes through said space between said first and second electrodes of said microorganism remover; and wherein said first electrode comprises a material having a higher oxidation-reduction potential than a material comprising the second electrode and at least said first electrode and said second electrode are arranged in contact with the water in said reservoir.

29. The humidifier in accordance with claim 1, wherein at least one of said first and said second electrodes has a through hole that allows said water to pass therethrough.

* * * * *